(12) United States Patent
Romeo

(10) Patent No.: US 7,301,635 B2
(45) Date of Patent: Nov. 27, 2007

(54) COLORIMETRIC METHOD FOR DETERMINING THE COLOR OF WINE

(76) Inventor: Jose Pascual Gracia Romeo, Calle Mayor, 91, Carineno, Zaragoza E-50400 (ES)

(*) Notice: Subject to any disclaimer, the term of this patent is extended or adjusted under 35 U.S.C. 154(b) by 754 days.

(21) Appl. No.: 10/381,305

(22) PCT Filed: Sep. 12, 2001

(86) PCT No.: PCT/ES01/00346

§ 371 (c)(1),
(2), (4) Date: Mar. 24, 2003

(87) PCT Pub. No.: WO02/29386

PCT Pub. Date: Apr. 11, 2002

(65) Prior Publication Data

US 2004/0037919 A1    Feb. 26, 2004

(30) Foreign Application Priority Data

Oct. 2, 2000   (ES)   ................... 200002375

(51) Int. Cl.
*G01N 21/25*   (2006.01)

(52) U.S. Cl. .................. 356/402; 356/300; 356/319
(58) Field of Classification Search ................ 356/300, 356/402

See application file for complete search history.

(56) References Cited

U.S. PATENT DOCUMENTS 3,935,317 A  *  1/1976  Bianchi ..................... 426/15

FOREIGN PATENT DOCUMENTS

ES          2117579       *   8/1998

* cited by examiner

*Primary Examiner*—F. L. Evans
(74) *Attorney, Agent, or Firm*—Foley & Lardner LLP

(57) ABSTRACT

The invention relates to a method for determining the color of wine from grapes. The method involves digesting the grapes in a pectolytic enzyme solution and a sulfur dioxide solution; diluting the solution with diluted acid and spectrophometric reading of the resulting solutions. The invention also relates to a program that calculates the probable color of the wine based on the spectroscopic data and physical-chemical parameters of the wine.

4 Claims, No Drawings

COLORIMETRIC METHOD FOR DETERMINING THE COLOR OF WINE

FIELD OF THE INVENTION

The present invention describes a process for the determination of the colour of wine from the grape. This process consists of digestion of the grapes with a solution of pectolytic enzymes and a solution of sulphurous anhydride, dilution of the solution with diluted acid and spectrophotometric reading of the resultant solution and a programme that calculates the wine's probable colour from spectroscopic data and physicochemical parameters of the wine.

BACKGROUND OF THE INVENTION

The wine's colour or intensity of colour is mainly caused by anthocyanins. There are trials and methods which take four hours that correlate the anthocyanin content in the grape with that of the wine. However, bulk wine on the market is paid by degree and point of colour and not by mg/l of anthocyanins; furthermore, there is not a high correlation (less than 0.5) between the colour degree and the anthocyanin content. Therefore, at present there is no suitable method for the determination of the intensity of the colour of wine from the grape.

OBJECT OF THE INVENTION

The present invention describes a method to predict the wine's probable colour, which will be obtained with the grapes analysed in a rapid and highly accurate way, by means of the extraction of colouring matter, spectrophotometric reading and exportation of the spectrophotometric data using a computer programme which, in turn, calculates the wine's probable colour from the spectrophotometric data and physicochemical parameters of the wine.

DETAILED DESCRIPTION OF THE INVENTION

The process to experimentally obtain the wine's probable colour consists of two parts:
a) Extraction of the colouring matter from the grapes and spectrophotometric measurement.
b) Calculation of the wine's colour from the spectrophotometric data and physicochemical parameters of the wine by means of a computer programme.

The seeded grapes can be digested at a temperature below 80° C. in the presence of a solution of pectolytic enzymes and an acid solution of sulphurous anhydride. Once extraction has finished, the mixture is purified, for which various different techniques such as flocculation, filtration or centrifugation can be used. The limpid solution is diluted with a diluted acid, preferably using hydrochloric acid. The resultant solution is read on a spectrophotometer in an interval of wavelengths between 280-700 nm.

A computer programme calculates the wine's probable colour from the spectrophotometric data and different analytical parameters of the wine fed into the programme. The analytical parameters are:
Total acidity
PH
Probable degree
Obtaining an accuracy of IC (real intensity of colour)=PC (Probable colour according to the process)±1.48

EXAMPLE

The invention is described by means of an example which does not limit the scope of the invention.

Example 1

This illustrates the method of extraction and the results obtained for different samples.

A 1% solution of pectolytic enzymes is added to 100 grams of seeded grapes, which is then triturated and an acid solution of sulphurous anhydride is added. The mixture is stirred at 80° C. for 10 minutes. 2 ml of the sample are centrifuged at 8000 rpm. The sample is diluted by 1/10 with diluted hydrochloric acid and a UV spectrum—visible between 200 and 700 nm—is performed.

Following official methods, the pH, alcohol content and total acidity are determined on the grapes.

In a parallel way, micro-vinifications are carried out to calculate the real value of the wine's colour intensity. The results obtained are shown below, where:
N is the sample number
P°D is the probable degree
TA is the total acidity
D280e and D520e are the absorbancies at 280 and 520 nm of the grape extract obtained for the probable colour determination.
ICv is the real intensity of colour of the wine obtained.
PC is the wine's intensity of colour, calculated according to the method.

| N | P° D | PH | TA | D280e | D520e | D280v | ICv | PC |
|---|---|---|---|---|---|---|---|---|
| 1 | 14.8 | 3.8 | 3.8 | 136 | 77 | 70 | 9.2 | 8.96 |
| 2 | 14.2 | 3.7 | 4.4 | 137 | 82 | 62 | 11.4 | 9.82 |
| 3 | 14.6 | 3.5 | 5.5 | 160 | 90 | 67 | 13.36 | 12.1 |
| 4 | 13.5 | 3.7 | 4.8 | 155 | 90 | 65 | 13.44 | 10.82 |
| 5 | 14.7 | 3.7 | 5.3 | 144 | 76 | 65 | 10.49 | 9.62 |
| 6 | 14.8 | 3.7 | 4.4 | 150 | 86 | 62 | 12.5 | 10.8 |
| 7 | 13.2 | 3.6 | 4.4 | 176 | 92 | 69 | 13.24 | 11.51 |
| 8 | 14.8 | 3.7 | 4.2 | 182 | 86 | 42 | 9.52 | 11.1 |
| 9 | 12.8 | 3.5 | 6.2 | 127 | 52 | 57 | 5.46 | 6.54 |
| 10 | 14.2 | 3.4 | 5.2 | 163 | 87 | 60 | 10.79 | 12.3 |
| 11 | 12.5 | 3.4 | 5.3 | 75 | 21 | 57 | 1.95 | 2.31 |
| 12 | 13.8 | 3.7 | 4.4 | 177 | 98 | 67 | 11.79 | 12.14 |
| 13 | 14.8 | 3.8 | 4.7 | 171 | 95 | 46 | 11.84 | 11.84 |
| 14 | 14.8 | 3.5 | 4.9 | 170 | 90.8 | 42.5 | 9.04 | 12.08 |
| 15 | 14.8 | 3.7 | 5.0 | 176 | 86 | 54 | 13 | 11.12 |
| 16 | 14.8 | 3.7 | 3.7 | 158 | 85 | 47.84 | 9.30 | 10.37 |
| 17 | 14.8 | 3.6 | 5.0 | 182 | 101 | 50 | 12.06 | 13.25 |
| 18 | 13.9 | 3.5 | 4.9 | 150 | 82 | 53 | 9.35 | 10.7 |
| 19 | 14.2 | 3.4 | 6.2 | 168 | 90.2 | 60.7 | 13.24 | 12.58 |
| 20 | 13.8 | 4.1 | 4.1 | 163 | 94 | 51 | 9.77 | 9.94 |
| 21 | 14.8 | 3.4 | 5.5 | 146 | 66 | 50 | 10.95 | 9.19 |
| 22 | 14.8 | 3.6 | 5.2 | 172 | 77 | 54 | 10.82 | 10.12 |
| 23 | 14.1 | 3.6 | 5.1 | 182 | 92 | 50 | 10.27 | 11.93 |
| 24 | 14.0 | 3.5 | 5.2 | 159 | 68 | 33 | 8.14 | 9.02 |
| 25 | 14.8 | 3.6 | 5.2 | 153 | 79 | 62 | 12.1 | 10.27 |
| 26 | 14.3 | 3.6 | 5.6 | 174 | 87 | 53 | 12.67 | 11.61 |
| 27 | 11.8 | 3.3 | 6.1 | 136.6 | 59 | 33 | 8.66 | 7.61 |
| 28 | 14.7 | 3.8 | 4.5 | 168 | 96 | 46 | 12.97 | 12.10 |
| 29 | 13.6 | 3.9 | 4.2 | 182 | 107 | 46 | 13.47 | 12.10 |
| 30 | 14.8 | 3.6 | 4.1 | 176 | 86 | 65 | 8.23 | 11.21 |
| 31 | 14.8 | 3.7 | 4.6 | 160 | 79 | 26 | 7.80 | 10.06 |
| 32 | 13.1 | 3.3 | 6.2 | 149 | 63 | 57 | 7.69 | 8.63 |
| 33 | 13.6 | 3.5 | 5.0 | 159 | 72 | 54 | 10.1 | 9.24 |
| 34 | 14.2 | 3.9 | 4.5 | 156 | 68 | 41 | 8.51 | 7.76 |
| 35 | 14.8 | 3.7 | 4.5 | 187 | 98.8 | 42 | 13.96 | 12.76 |
| 36 | 14.8 | 3.8 | 5.0 | 123 | 63 | 44 | 5.83 | 7.40 |
| 37 | 14.8 | 3.6 | 4.2 | 188 | 100 | 51 | 13.46 | 13.24 |
| 38 | 14.8 | 3.8 | 4.4 | 180 | 98 | 51 | 10.34 | 12.11 |
| 39 | 14.8 | 3.8 | 4.5 | 166 | 74 | 59 | 7.50 | 8.86 |

-continued

| N | P° D | PH | TA | D280e | D520e | D280v | ICv | PC |
|---|------|-----|-----|-------|-------|-------|-------|-------|
| 40 | 14.8 | 3.7 | 5.9 | 141 | 68 | 34 | 9.14 | 8.53 |
| 41 | 14.8 | 3.8 | 4.3 | 148 | 81 | 36 | 8.52 | 9.75 |
| 42 | 14.8 | 3.7 | 5.5 | 151 | 77 | 39 | 10.35 | 9.63 |
| 43 | 14.2 | 3.7 | 4.6 | 151 | 67 | 43 | 10.78 | 8.41 |
| 44 | 14.8 | 3.6 | 3.9 | 191 | 105 | 38 | 15.25 | 13.58 |
| 45 | 14.8 | 3.6 | 5.5 | 144 | 78 | 64 | 7.56 | 10.13 |
| 46 | 14.5 | 3.6 | 3.5 | 206 | 98 | 37 | 10.64 | 13.09 |
| 47 | 13.5 | 3.6 | 5.5 | 146 | 71 | 58 | 9.32 | 9.02 |
| 48 | 12.9 | 3.7 | 5.1 | 141 | 80 | 49 | 9.29 | 9.39 |
| 49 | 14.8 | 3.8 | 4.7 | 195 | 105 | 53 | 11.48 | 13.05 |
| 50 | 13.1 | 3.7 | 4.4 | 155 | 80 | 49 | 9.67 | 9.39 |
| 51 | 12.4 | 3.7 | 3.8 | 165 | 87 | 43 | 9.37 | 9.96 |
| 52 | 14.0 | 3.6 | 5.1 | 211 | 93 | 50 | 12.5 | 12.53 |
| 53 | 13.6 | 3.7 | 4.6 | 160 | 88 | 29 | 8.68 | 10.68 |
| 54 | 14.8 | 3.9 | 4.1 | 194 | 97 | 49 | 11.00 | 12.01 |
| 55 | 14.8 | 3.7 | 4.4 | 161 | 83 | 58 | 10.0 | 10.41 |
| 56 | 14.6 | 3.9 | 4.0 | 162 | 100 | 60 | 12.06 | 11.50 |
| 57 | 14.7 | 3.6 | 4.9 | 212 | 111 | 65 | 12.24 | 15.23 |
| 58 | 13.8 | 3.9 | 6.0 | 155 | 84 | 47 | 7.79 | 9.92 |
| 59 | 14.2 | 3.7 | 4.6 | 164 | 81 | 47 | 9.91 | 10.17 |
| 60 | 13.9 | 3.5 | 6.0 | 133 | 59 | 45 | 3.70 | 7.60 |
| 61 | 13.2 | 3.7 | 4.6 | 148 | 61 | 69 | 5.93 | 7.28 |
| 62 | 14.8 | 3.7 | 4.6 | 170 | 74 | 31 | 8.82 | 9.46 |
| 63 | 14.8 | 3.7 | 4.6 | 161 | 64 | 23 | 10.00 | 8.09 |
| 64 | 14.8 | 3.7 | 4.6 | 182 | 88 | 70.2 | 12.17 | 11.35 |
| 65 | 14.8 | 3.8 | 4.2 | 182 | 79 | 62 | 10.31 | 10.03 |
| 66 | 12.6 | 4.0 | 4.1 | 160 | 84 | 67 | 9.66 | 8.91 |
| 67 | 13.7 | 3.6 | 4.6 | 171 | 74 | 65 | 10.76 | 9.50 |
| 68 | 14.5 | 3.7 | 5.1 | 153 | 63 | 65 | 9.22 | 7.97 |
| 69 | 14.5 | 3.6 | 5.0 | 160 | 75 | 62 | 10.83 | 9.69 |

The invention claimed is:

1. A colorimetric process for determination of the colour of wine from a grape, comprising:
   a) extraction from the grape a portion of colouring matter of the grape in a solution of pectolytic enzymes at a temperature below 80° C. in the presence of an acid solution of sulphurous anhydride;
   b) purification of the extraction mixture;
   c) dilution of the solution with a diluted acid;
   d) reading of the resultant solution by using a spectrophotometer in an interval of wavelengths between 280-700 nm,
   e) obtaining pH, total acidity, and probable degree of the grape, and
   f) calculation of the wine's probable colour from spectroscopic data, pH, total acidity, and probable degree, by means of a computer program,
   g) reporting of the probable colour in a user readable format.

2. A colorimetric method for determining the probable colour of wine from a grape, the process comprising:
   extracting at least a portion of colouring matter of the grape in an acidic solution of pectolytic enzymes and sulphurous anhydride at a temperature below 80°C. to yield an extraction mixture;
   purifying the extraction mixture;
   diluting the purified extraction mixture with a diluted acid;
   measuring spectroscopic properties of the diluted extraction mixture by using a spectrophotometer in an interval of wavelengths between 280-700 nm, and
   obtaining pH, total acidity, and probable degree of the grape;
   calculating the wine's probable colour from the spectroscopic data, pH, total acidity, and probable degree by means of a computer program; and
   reporting the probable colour calculated by the computer program.

3. The method of claim 2, wherein the dilute acid is hydrochloric acid.

4. The method of claim 2, wherein the step of measuring spectroscopic properties of the diluted extraction mixture includes measuring the absorbance of the diluted extraction mixture at about 280 nm and about 520 nm.

* * * * *